(12) United States Patent
Seeger et al.

(10) Patent No.: US 7,708,015 B2
(45) Date of Patent: May 4, 2010

(54) PROCESS FOR THE AUTOMATIC RECORDING OF PRESSURE-VS.-VOLUME CURVES DURING ARTIFICIAL RESPIRATION

(75) Inventors: Dieter Seeger, Hamburg (DE); Ralf Lorenzen, Lübeck (DE); Hans-Joachim Kohl, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 957 days.

(21) Appl. No.: 11/168,713

(22) Filed: Jun. 28, 2005

(65) Prior Publication Data

US 2006/0037616 A1 Feb. 23, 2006

(30) Foreign Application Priority Data

Aug. 17, 2004 (DE) ........................ 10 2004 039 711

(51) Int. Cl.
*A61M 16/00* (2006.01)
*A61H 31/00* (2006.01)
*A62B 7/00* (2006.01)

(52) U.S. Cl. ............................ 128/204.23; 128/204.18; 128/204.21; 128/204.26; 128/204.29; 128/207.14

(58) Field of Classification Search ............ 128/204.23, 128/204.21, 204.24, 204.18, 204.22, 200.24, 128/203.14, 203.24; 600/529, 538
See application file for complete search history.

(56) References Cited

U.S. PATENT DOCUMENTS

| | | | |
|---|---|---|---|
| 3,234,932 A * | 2/1966 | Bird et al. ............... | 128/204.25 |
| 3,480,006 A * | 11/1969 | Schomber ................... | 600/533 |
| 3,664,370 A | 5/1972 | Warnow | |
| 3,820,566 A * | 6/1974 | Sundblom et al. ....... | 137/624.14 |
| 3,923,056 A * | 12/1975 | Bingmann et al. ..... | 128/204.21 |
| 3,961,627 A | 6/1976 | Ernst et al. | |
| 4,448,192 A | 5/1984 | Stawitcke et al. | |

(Continued)

FOREIGN PATENT DOCUMENTS

DE     1912829     10/1970

(Continued)

OTHER PUBLICATIONS

Servillo et al., "Pressure-Volume Curves in Acute Respiratory Failure", Am J Respir Crit Care Med 155:1629-1636, 1997.

(Continued)

*Primary Examiner*—Steven O Douglas
*Assistant Examiner*—Clinton Ostrup
(74) *Attorney, Agent, or Firm*—McGlew and Tuttle, P.C.

(57) ABSTRACT

A process, system and device are provided for automatically recording pressure-vs.-volume curves during artificial respiration with a respirator. The inspiration pressure is increased during the supply of a breathing gas volume flow under the control of a control unit. The resulting breathing gas volume flow rate is detected and the volume is determined from the latter by integration. The control unit compares the breathing gas volume flow detected during the phase of expiration with a preselected set point and acts on an expiration valve (12) in the expiration line (8) by means of a controller in case of deviation from the set point in order to return the breathing gas volume flow to the set point.

19 Claims, 4 Drawing Sheets

U.S. PATENT DOCUMENTS

| | | | | |
|---|---|---|---|---|
| 4,838,257 | A | * | 6/1989 | Hatch ................... 128/204.21 |
| 4,928,684 | A | | 5/1990 | Breitenfelder et al. |
| 5,094,235 | A | | 3/1992 | Westenskow et al. |
| 5,320,093 | A | * | 6/1994 | Raemer ................ 128/203.12 |
| 5,471,977 | A | | 12/1995 | Olsson et al. |
| 5,540,220 | A | * | 7/1996 | Gropper et al. ........ 128/204.21 |
| 5,575,283 | A | * | 11/1996 | Sjoestrand ............ 128/204.23 |
| 5,582,163 | A | * | 12/1996 | Bonassa .............. 128/204.26 |
| 5,664,562 | A | | 9/1997 | Bourdon |
| 5,740,796 | A | * | 4/1998 | Skog .................... 128/204.23 |
| 5,797,393 | A | * | 8/1998 | Kohl .................... 128/204.23 |
| 5,810,002 | A | | 9/1998 | Dittmann |
| 6,269,812 | B1 | * | 8/2001 | Wallace et al. ......... 128/205.23 |
| 6,279,574 | B1 | * | 8/2001 | Richardson et al. .... 128/204.18 |
| 6,626,175 | B2 | * | 9/2003 | Jafari et al. ........... 128/204.21 |
| 6,668,824 | B1 | * | 12/2003 | Isaza et al. ............ 128/202.22 |
| 6,718,975 | B2 | | 4/2004 | Blomberg |
| 6,729,343 | B2 | * | 5/2004 | Ludwig et al. ................ 137/14 |
| 6,739,336 | B1 | * | 5/2004 | Jalde et al. ............ 128/204.21 |
| 7,549,421 | B2 | * | 6/2009 | Levi et al. ............. 128/204.21 |
| 2004/0231673 | A1 | * | 11/2004 | Reissmann ............ 128/207.14 |
| 2006/0037616 | A1 | * | 2/2006 | Seeger et al. .......... 128/204.23 |
| 2006/0211950 | A1 | * | 9/2006 | Brunner et al. ........ 128/204.18 |

FOREIGN PATENT DOCUMENTS

| | | |
|---|---|---|
| DE | 2314356 | 10/1973 |
| DE | 2441306 | 3/1975 |
| DE | 3306607 | 9/1983 |
| DE | 3817985 | 12/1989 |
| DE | 4004034 | 11/1990 |
| DE | 19639522 | 4/1998 |
| DE | 69318982 | 11/1998 |
| DE | 10114628 | 9/2002 |
| EP | 0570612 | 11/1993 |
| EP | 1269914 | 1/2003 |
| GB | 1 432 572 | 4/1976 |
| WO | WO 03/037413 A1 | 5/2003 |
| WO | WO03037413 | 5/2003 |

OTHER PUBLICATIONS

Jandre FC et al., A closed-loop mechanical ventilation controller with explicit objective functions, IEEE Trans Biomed Eng 51(5): 823-831, May 2004.

Veiellard-Baron A et al., Early patterns of static pressure-volume loops in ARDS and their relations with PEEP-induced recruitment. Intensive Care Med 29(11): 1929-1935, 2003.

Bottino DA, et al., Decision support system to assist mechanical ventilation in the adult respiratory distress syndrome, Int J Clin Monit Comput 14(2): 73-81, 1997.

Blanc Q. et al., Inspiratory pressure-volume curves obtained using automated low constant flow inflation and automated occlusion methods in ARDS patients with a new device. Intensive Care Med 28 (7): 990-994, 2002.

Servillo G et al., The upper inflection point of the pressure-volume curve. Influence of methodology and of different modes of ventilation. Intensive Care Med 28 (7): 842-849, 2002.

* cited by examiner

PROCESS FOR THE AUTOMATIC RECORDING OF PRESSURE-VS.-VOLUME CURVES DURING ARTIFICIAL RESPIRATION

CROSS REFERENCE TO RELATED APPLICATIONS

This application claims the benefit of priority under 35 U.S.C. §119 of German Application DE 10 2004 039 711.2 filed Aug. 17, 2004, the entire contents of which are incorporated herein by reference.

FIELD OF THE INVENTION

The present invention pertains to a process for the automatic recording of pressure-vs.-volume curves during artificial respiration with a respirator, in which the inspiration pressure is increased during the supply of a breathing gas volume flow under the control of a control means, the resulting breathing gas volume flow is detected, and the volume is determined from the latter by integration. The present invention pertains, furthermore, to a device for carrying out the process.

BACKGROUND OF THE INVENTION

A PV curve (PV loop) is run through during the artificial respiration of intubated patients who are not breathing spontaneously and this is used to measure the lung. For example, a volume that is usually substantially larger than the maximum volume normally applied during the current respiration is applied in this case. This volume is subsequently expired again. The volume and the pressure are recorded during the inspiration and expiration in an X-Y plot (curve). The so-called inflection points (opening and closing points) of the lungs, the so-called lung compliance at different pressures and other measured variables can then be determined from this curve in order to then optimize the respiration pressures of the current respiration.

A process of the type described in the introduction is known, for example, from the document WO 03/037413 A1. A prolonged phase of expiration is carried out in the process described there before the PV manoeuver in order to lower the pressure to a preset minimum value, which is the so-called positive end expiratory pressure (PEEP). The inspiration pressure is then increased continuously over a pressure ramp to a preset peak pressure and the volume is determined at the same time, which is possible, e.g., by detecting the breathing gas volume flow and by integrating same. A passive expiration to the end pressure is carried out after the manoeuver described. The pressure curve is then plotted as a two-dimensional curve against the volume. The PV curve can then be analyzed in the known manner, and the normal breathing cycles can be continued with the respirator. Furthermore, the possibility of allowing the pressure to drop from the preset maximum over a pressure ramp to the desired minimum in a controlled manner is addressed. Based on the nonlinear flow behavior of the lungs, a more or less greatly varying breathing gas volume flow with peaks is now obtained.

One problem in the prior-art PV measurement maneuvers is that they ignore the fact that a pressure drop is also brought about by flow resistances of the breathing gases in the airways and in the lungs. However, these effects on the PV curve obtained, which are due to the flow resistance, cannot be ignored any longer in case of larger breathing gas volume flows. Even though it would be possible to avoid this problem by running through a slow pressure rise ramp and a correspondingly slow expiration curve, this would require an excessively long measuring time and unduly stress the patient.

SUMMARY OF THE INVENTION

The object of the present invention is to provide a process for recording PV curves during artificial respiration with a respirator, with which the PV curve of the lung can be recorded with a greater accuracy and gently for the patient.

According to the invention, a process is provided for the automatic recording of pressure-volume curves during artificial respiration with a respirator, in which the inspiration pressure is increased during the supply of a breathing gas volume flow under the control of a control unit, the resulting breathing gas volume flow is detected and the volume is determined from the latter by integration. Provisions are made according to the present invention for the breathing gas volume flow to be detected during the phase of expiration and to be compared in the control unit with a preselected set point. If the breathing gas volume flow detected deviates from the preselected set point, a controller implemented in the control unit acts on a valve arranged downstream in the expiration line in order to return the breathing gas volume flow to the set point. The breathing gas volume flow is also called "flow."

Volume flow peaks, at which the pressure components that are due to the flow resistance cannot be ignored, can thus be prevented from occurring, and a more accurate PV curve can thus be obtained.

Due to the fact that the medical staff is enabled to preset the set point of the breathing gas volume flow during the phase of expiration, the staff can select whether a high accuracy of measurement is preferred (in case of a set point set at a rather low value) compared with a longer phase of expiration or whether a somewhat lower accuracy is given preference compared with a shorter phase of expiration. The staff can thus run through the most suitable PV manoeuver for each patient.

After the PV measuring manoeuver has been performed and the PV curve has been recorded, a plurality of parameters are determined from it in the usual manner, and this evaluation also determines parameters automatically, and this evaluation can also be carried out automatically in the control unit. The normal breathing cycles are continued after such a recording of the PV curve, and the control unit can take into account the curve parameters determined during the evaluation of the PV curve.

The recording of the PV curve can be started by the staff manually. The breathing parameters necessary for the recording of a PV curve can also be suggested from an expert system, which evaluates data of preceding measurements or measured values of the current respiration.

The controller, which records the measured value for the breathing gas volume flow in the expiration line and exerts a regulating action on the valve in the expiration line, can be provided in the control unit by programming. Such a controller may be, e.g., a so-called proportional-integral controller (PI controller).

If the valve in the expiration line is sensitive to vibrations, which prohibits excessively rapidly reacting control, it may be preferable to store measured pressure values during the inspiration with essentially constant breathing gas volume flow and to use the pressure curve thus determined during the phase of expiration as an anticipatory control for the controller.

In a preferred device for carrying out the process, an expiration valve, which is designed as a diaphragm valve and is controlled by the control unit electropneumatically, is provided in the expiration line upstream of a breathing gas volume flow sensor for detecting the breathing gas volume flow.

The present invention will be described below on the basis of an exemplary embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
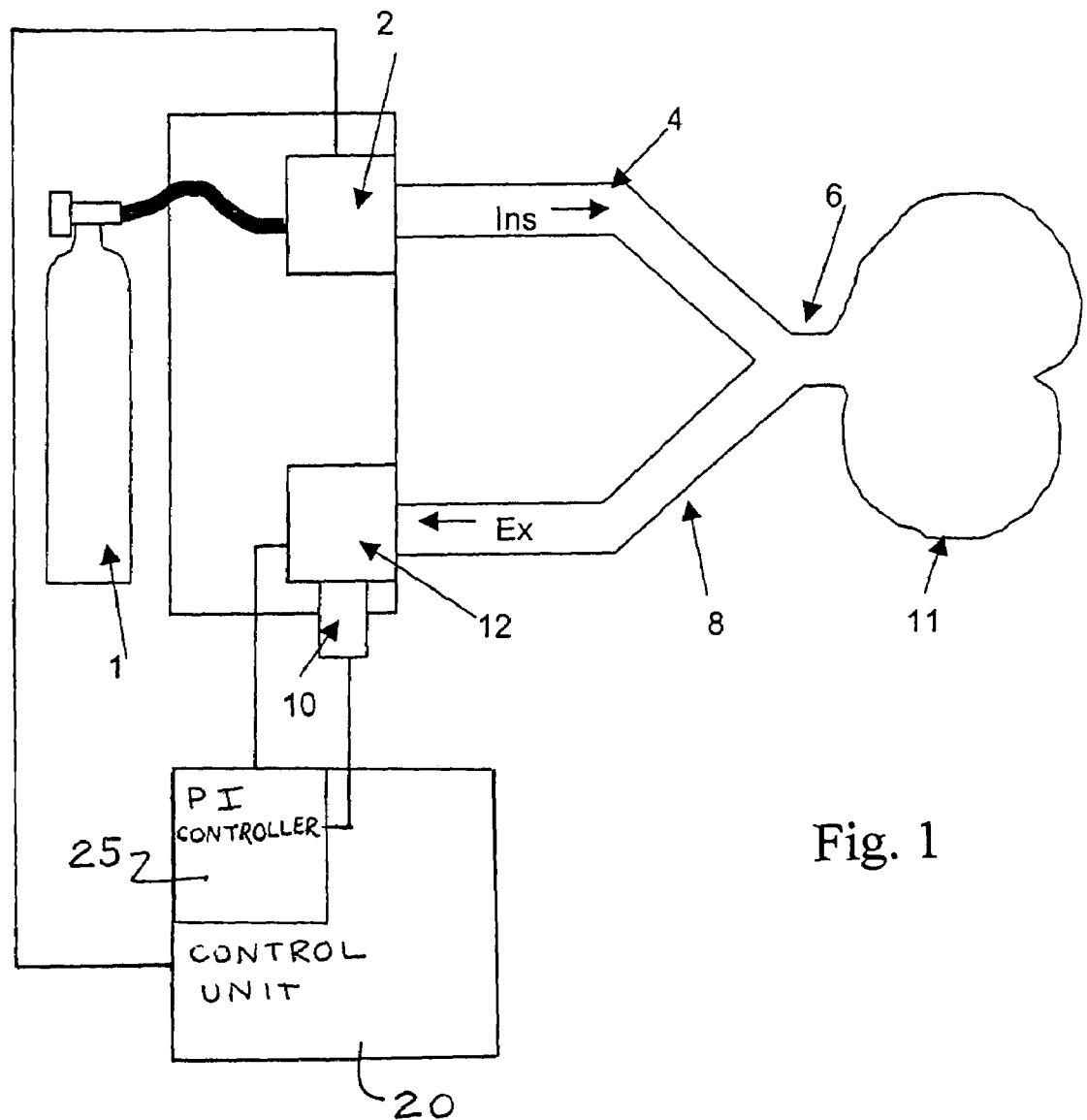
FIG. 1 is a schematic view of a respirator suitable for the process according to the present invention.

Referring to the drawings in particular, FIG. 1 schematically shows a respirator, which schematically shows only the components that are significant in connection with the present invention. The respirator is connected with a breathing gas source 1, which is connected with a source 2 for the breathing gas volume flow, which said source 2 can be readily set. The source 2 for the breathing gas volume flow is joined by an inspiration line 4, which is connected with the patient and an expiration line 8 via a Y-piece 6. The patient's lungs are designated by 11.

The expiration line 8 is connected with an expiration valve 12, from which the breathing gas volume flow flowing out flows through a breathing gas volume flow sensor 10.

Furthermore, a control unit 20 (shown schematically), which may be designed as a programmable processor unit, is present in the respirator. This control unit 20 may be set up for carrying out the process according to the present invention, besides the performance of the normal breathing cycles, in order to carry out a PV maneuver to record the PV curve of the lungs 11. The control unit 20 is connected for this purpose with a breathing gas volume flow sensor 10 and is programmed with a controller function. This controller function acts on the expiration valve in order to maintain the breathing gas volume flow essentially at a preset set point during the phase of expiration. This set point can be set by a user on the respirator.

Figure 2:
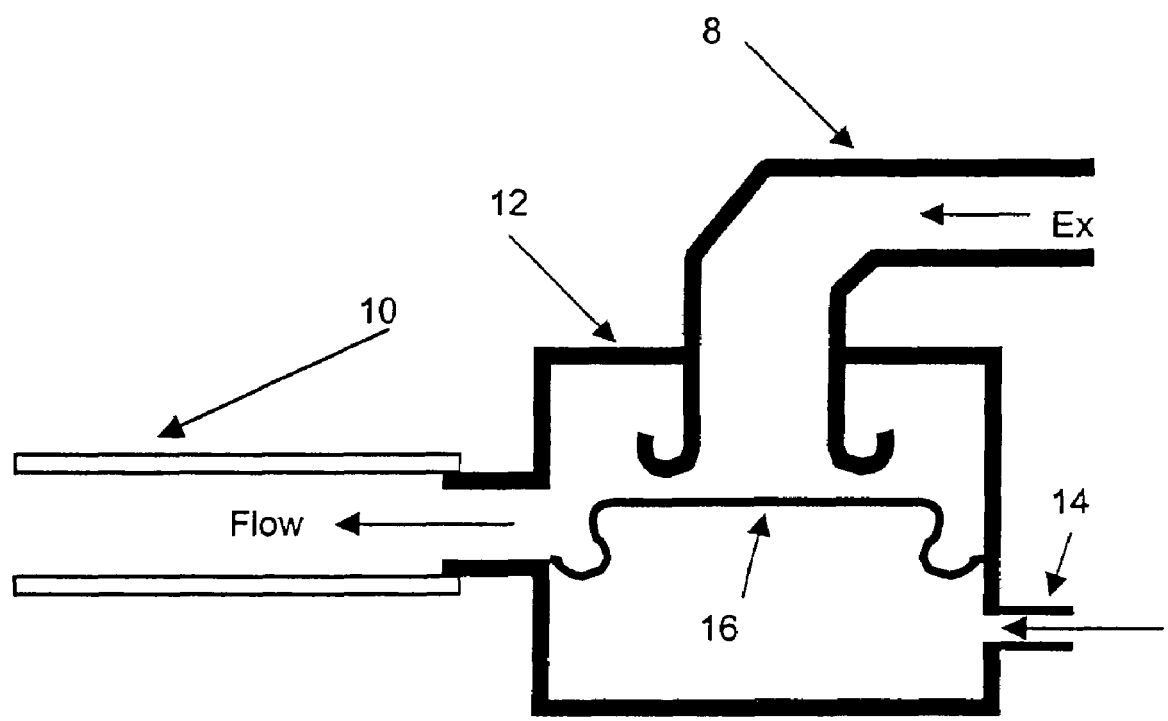
FIG. 2 shows a schematic cross-sectional view of a valve in the expiration line of the respirator from FIG. 1.

An embodiment of the expiration valve 12 is schematically shown in FIG. 2. The expiration line 8 opens into a housing of an expiration valve 12, which is designed as a diaphragm valve. The diaphragm 16 of the valve divides the housing, and a valve chamber is supplied via a line 14 with control pressure, which is preset by the control unit 20 of the respirator. The breathing gas volume flow flows through the opposite chamber of the valve housing during the phase of expiration. By increasing the control pressure acting on the diaphragm 16, the flow resistance for the breathing gas volume flow flowing off is increased, and this breathing gas volume flow is reduced as a result. A breathing gas volume flow sensor 10, which is coupled with the control unit 20 of the respirator, is connected to the outlet of the expiration valve 12.

A controller 25, which receives the output signal of the breathing gas volume flow sensor 10 and sends a control signal, which is used to control the expiration valve 12 in such a way that the breathing gas volume flow ("flow") flowing off will be kept as close to the set point set as possible, is implemented in the control unit. The controller may be designed, for example, as a proportional-integral controller (PI controller). To avoid possible vibrations in the expiration flow, absorbing means may be provided, or the measured pressure values are recorded during the phase of inspiration, which is preferably carried out with constant supply of a breathing gas volume flow, and this pressure curve can be used to create an anticipatory control for the controller.

Figure 3:
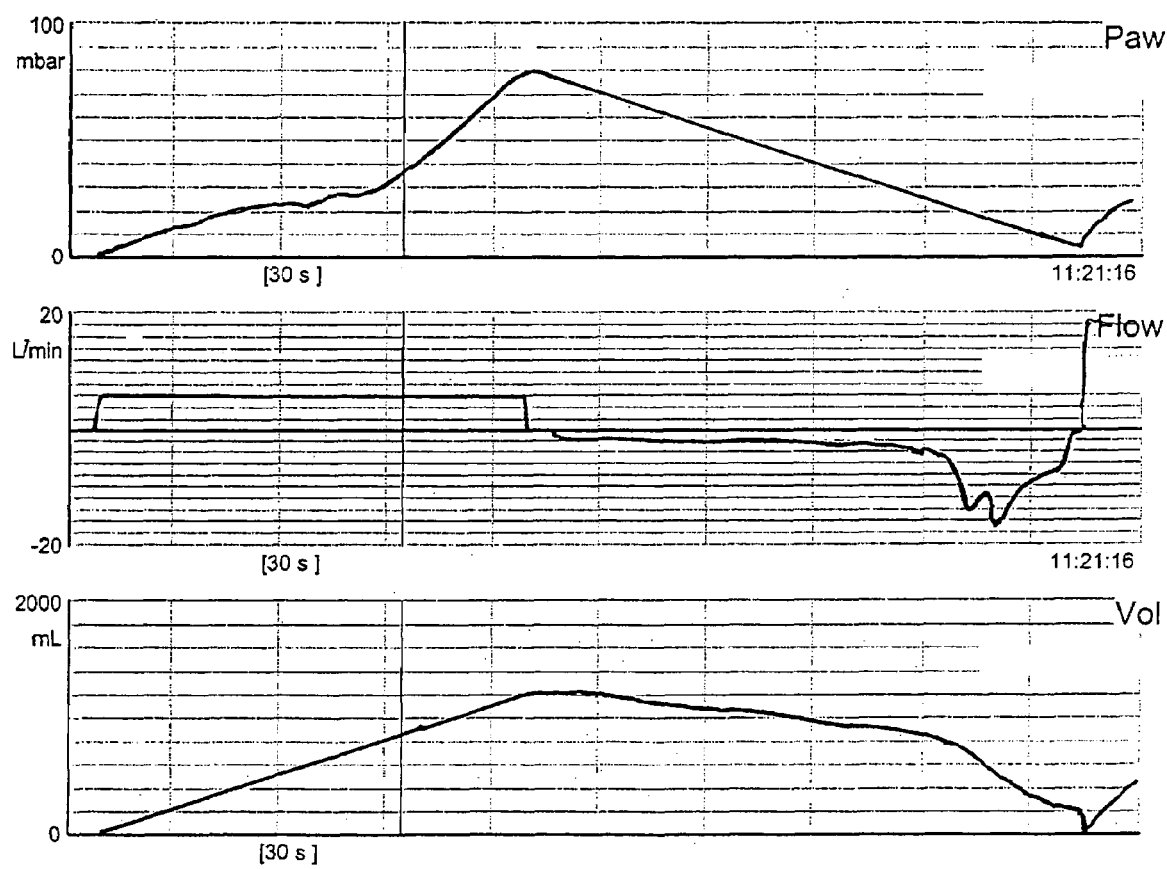
FIG. 3 shows the curve of the pressure, breathing gas volume flow and volume during a PV manoeuver, during which the pressure is lowered essentially linearly during the phase of expiration in the conventional manner.

FIG. 3 shows at first the curves of the pressure ("Paw"), the breathing gas volume flow ("flow") and the volume ("Vol") for a PV manoeuver, in which the pressure is lowered essentially linearly during the phase of expiration over a pressure ramp. As can be determined from the diagram of the breathing gas volume flow in the middle, this breathing gas volume flow increases greatly by the end of the phase of expiration, and the measurement of the PV curve is distorted here because of the flow resistances.

Figure 4:
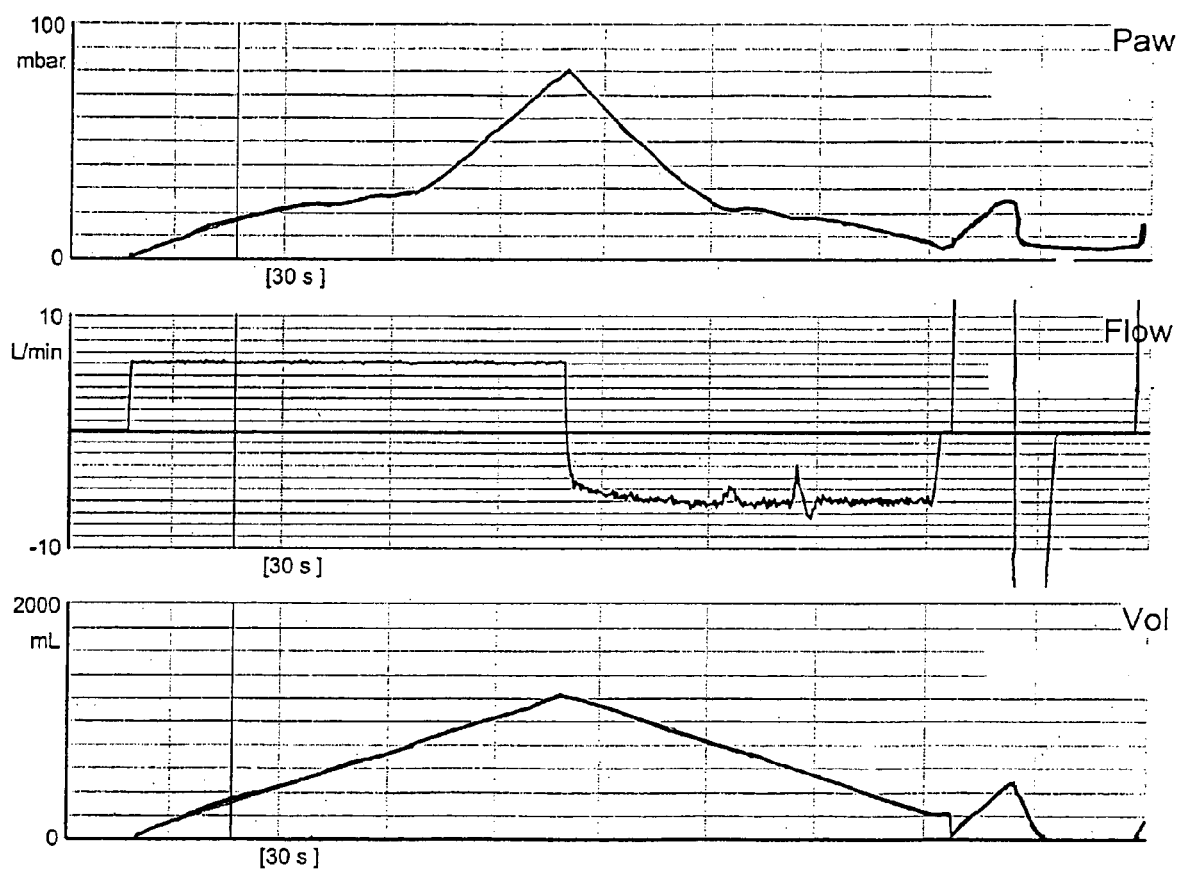
FIG. 4 shows the corresponding curves during a PV manoeuver according to the present invention, in which the breathing gas volume flow is controlled during the phase of expiration essentially to a constant volume flow.

By contrast, the corresponding curves in FIG. 4 are shown for a PV manoeuver according to the present invention, in which the breathing gas volume flow flowing out is detected and this measured value is coupled to the control unit in order to keep the breathing gas volume flow essentially constant during the phase of expiration. As can be determined from the diagram in the middle, the breathing gas volume flow remains essentially at the set point of, for example, 6.0 L per minute during the phase of expiration without showing the undesired breathing gas volume peaks at the end.

The next normal breathing cycle, which covers a substantially smaller PV range than the preceding PV manoeuver for recording the PV curve, can be seen in FIG. 4 following the expiration phase of the PV manoeuver.

As can be determined from the curve in the middle in FIG. 4, the PV manoeuver according to the present invention is preferably carried out such that the source 2 for the breathing gas volume flow is controlled by the control unit such that it delivers a constant breathing gas volume flow during the phase of inspiration. This can be achieved by suitably controlling a valve in the source 2 for the breathing gas volume flow by the control unit.

While a specific embodiment of the invention has been shown and described in detail to illustrate the application of the principles of the invention, it will be understood that the invention may be embodied otherwise without departing from such principles.

What is claimed is:

1. A process for the automatic recording of pressure-volume (PV) curves during artificial respiration with a respirator having an inspiration line and an expiration line, the process comprising the steps of:

during an inspiration phase increasing inspiration pressure values during the supply of a breathing gas volume flow under the control of a control unit;

detecting breathing gas volume flow values of the breathing gas volume flow;

determining volume values of the breathing gas volume flow from the detected breathing gas volume flow values by integration of the detected breathing gas volume flow values over time;

during an expiration phase acting on an expiration valve in the expiration line by means of the control unit in case of deviation of a detected expiration phase breathing gas volume flow from a preselected expiration breathing gas volume flow set point in order to return breathing gas volume flow to the set point during said expiration phase; and recording breathing gas pressure values and volume values during inspiration and expiration to record a PV curve.

2. A process in accordance with claim 1, wherein a proportional-integral (PI) controller is used as the control function of the control unit.

3. A process in accordance with claim 1, wherein the breathing gas volume flow is essentially constant during the phase of inspiration.

4. A process in accordance with claim 1, wherein said inspiration pressure values are stored during the phase of inspiration and a pressure curve determined from said stored pressure values is used during the phase of expiration for anticipatory control for the controller.

5. A process in accordance with claim 1, wherein the PV curve is recorded by means of the control unit and an expert system suggests respiration parameters necessary for recording the PV curve.

6. A process in accordance with claim 1, wherein the recording of the PV curve is started manually.

7. A process in accordance with claim 1, wherein the control unit automatically, after the recording of the PV curve, determines parameters of the curve, and the control unit subsequently automatically continues controlling breathing cycles based on the determined parameters of the curves.

8. A process in accordance with claim 1, wherein the expiration valve comprises a diaphragm valve and is electropneumatically controlled by said control unit, said expiration valve being provided in the expiration line upstream of a breathing gas volume flow sensor for detecting the breathing gas volume flow.

9. A device for the automatic recording of pressure-volume curves during artificial respiration with a respirator, the device comprising:
an inspiration line;
an expiration line;
an expiration valve acting in the expiration line;
a control unit with a controller;
a pressure settable breathing gas supply that can increase inspiration pressure during the supply of a breathing gas volume flow under the control of the control unit;
a breathing gas volume flow sensor for detecting breathing gas volume flow, said control unit determining the volume from the detected breathing gas volume flow by integration and during a phase of expiration comparing the breathing gas volume flow detected during said phase of expiration with a preselected expiration breathing gas volume flow set point and during said phase of expiration acting on said expiration valve in case of deviation from the set point in order to return the breathing gas volume flow to the set point during said phase of expiration.

10. A device in accordance with claim 9, wherein said breathing gas volume flow sensor is in said expiration line and said expiration valve comprises a diaphragm valve and is electropneumatically controlled by said control unit, said expiration valve being provided in said expiration line upstream of said breathing gas volume flow sensor for detecting the breathing gas volume flow.

11. A respirator system for automatic recording of a pressure-volume data during artificial respiration, the system comprising:
an inspiration line;
an expiration line;
an expiration valve acting in the expiration line;
a control unit;
a pressure settable breathing gas supply that can increase inspiration pressure during the supply of a breathing gas volume flow under the control of said control unit;
a breathing gas volume flow sensor for detecting breathing gas volume flow values in said expiration line, said control unit for determining the volume from the detected breathing gas volume flow by integration of said breathing gas volume flow values over time for acting on said expiration valve in case of deviation of the breathing gas volume flow detected during an expiration phase from a preselected expiration breathing gas volume flow set point in order to return the breathing gas volume flow to the set point during said expiration phase.

12. A respirator system in accordance with claim 11, wherein a proportional-integral (PI) controller is used for said acting on said expiration valve in case of deviation of the breathing gas volume flow detected during an expiration phase from a preselected expiration breathing gas volume flow set point in order to return the breathing gas volume flow to the set point during said expiration phase.

13. A respirator system in accordance with claim 11, wherein an essentially constant breathing gas volume flow is supplied during the phase of inspiration.

14. A respirator system in accordance with claim 11, wherein measured pressure values are stored during the phase of inspiration and a pressure curve determined from said stored pressure values is used during the phase of expiration for anticipatory control for the controller.

15. A respirator system in accordance with claim 11, wherein a pressure-volume (PV) curve is recorded by means of the control unit, which suggests the respiration parameters necessary for recording the PV curve, and data of preceding measurements or measured values of the current respiration are evaluated.

16. A respirator system in accordance with claim 11, wherein a recording of a pressure-volume (PV) curve is started manually.

17. A respirator system in accordance with claim 11, wherein the control unit automatically, after the recording of the PV curve, determines parameters of the curve, and subsequently automatically continues with breathing cycles based on the determined parameters of the curves.

18. A respirator system in accordance with claim 11, wherein said expiration valve comprises a diaphragm valve and is electropneumatically controlled by said control unit, said expiration valve being provided in said expiration line upstream of said breathing gas volume flow sensor for detecting the breathing gas volume flow.

19. A process for recording pressure-volume (PV) curves during artificial respiration with a respirator having an inspiration line and an expiration line operatively connected to the lungs of the patient, the process comprising the steps of:
performing a PV maneuver including a phase of inspiration and followed by a phase of expiration and including initiating the PV maneuver by increasing inspiration pressure during the supply of a breathing gas volume flow under the control of a control unit and with the control unit controlling the pressure to pressure values;

detecting a resulting breathing gas volume flow values during the PV maneuver;

providing volume values by integration of said detected breathing gas volume flow values over time;

providing an expiration valve in an expiration line;

during said phase of expiration, acting on the expiration valve in the expiration line to return the breathing gas volume flow to a set point value during said phase of expiration upon the detected breathing gas volume flow value deviating from the set point value during said phase of expiration; and recording the pressure values and volume values of the PV maneuver.

* * * * *